United States Patent [19]
Ohashi et al.

[11] Patent Number: 5,814,818
[45] Date of Patent: Sep. 29, 1998

[54] GAS TUBE FOR PASSING PLASMA GENERATING GASES

[75] Inventors: Toshio Ohashi, Komaki; Michio Asai, Nagoya, both of Japan

[73] Assignee: NGK Insulators, Ltd., Japan

[21] Appl. No.: 869,920

[22] Filed: Jun. 5, 1997

[30] Foreign Application Priority Data

Jun. 11, 1996 [JP] Japan ................................. 8-149232

[51] Int. Cl.⁶ .................................................. G01N 21/17
[52] U.S. Cl. ..................................... 250/432 R; 250/428
[58] Field of Search ............................... 250/432 R, 435, 250/428

[56] References Cited

U.S. PATENT DOCUMENTS 5,486,904  1/1996  Horn et al. ......................... 250/432 R Primary Examiner—Kiet T. Nguyen
Attorney, Agent, or Firm—Parkhurst & Wendel, LLP

[57] ABSTRACT

A gas tube for passing plasma generating gases, having high UV transmittance and corrosion resistance against corrosive gases is disclosed. The tube is composed of a longitudinally extended throughhole and a thin circumferential wall and is provided with a means for radiating UV rays directed to an upstream portion thereof from outside. The wall is formed of a light-pervious alumina ceramic, and has a center-line mean roughness ($R_a$) of not more than 1.0 $\mu$m in a portion exposed to gas plasma.

6 Claims, 2 Drawing Sheets

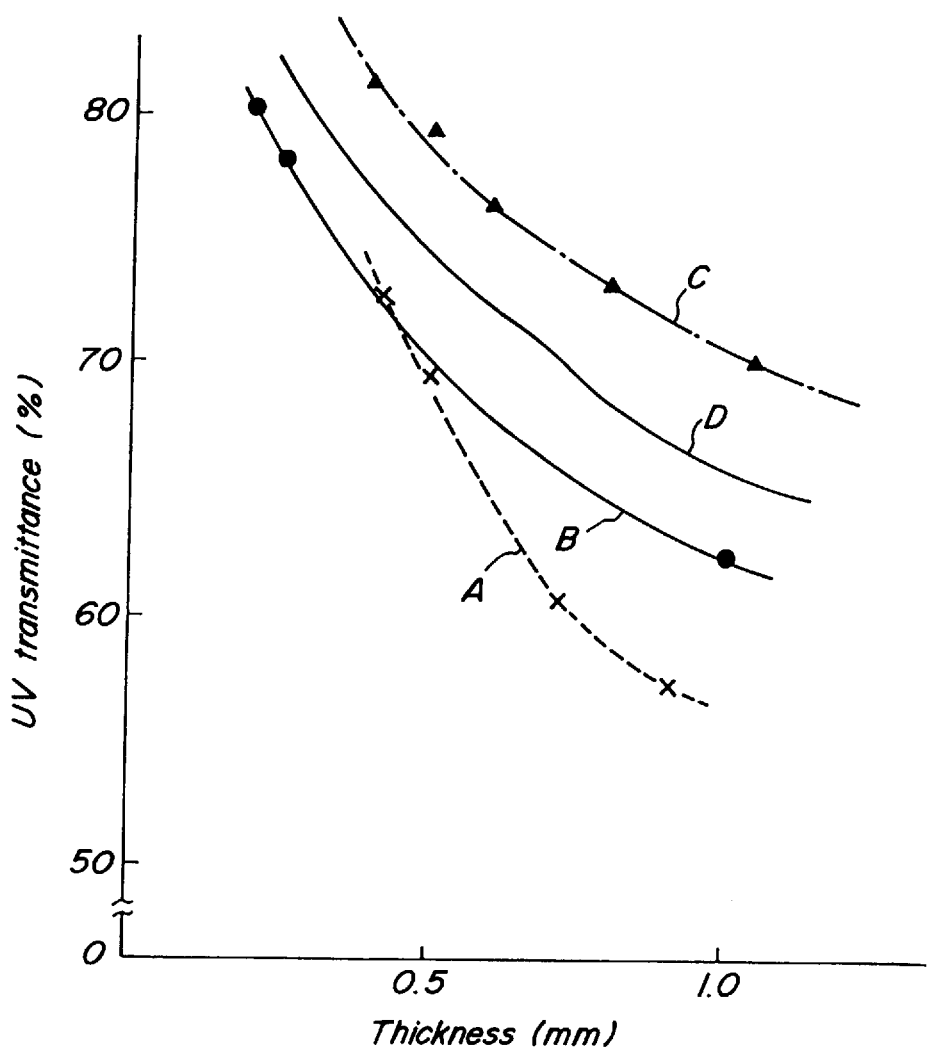

GAS TUBE FOR PASSING PLASMA GENERATING GASES

BACKGROUND OF THE INVENTION

1. Field of the Invention

The present invention relates to a gas tube for passing a gas for generating plasma therethrough and irradiating the running gas with ultraviolet (UV) rays therein.

2. Description of Related Art

Recently, use of plasma treating apparatuses having high efficiency and precision has been increasing with rapid development of micronization of semiconductor patterns. For example, gas plasma is used for forming micropatterns by means of selective etching of a membrane which has been formed on a substrate to be treated. When the gas plasma is generated, gas is ionized to produce radicals on gas constituent molecules. Then, the radicals impinge and react upon the substrate to be treated. Radicals are classified into ion radicals and neutral radicals, both of which are so active that gas phase growth and dry etching can effectively proceed.

As materials for the gas tubes for passing plasma generating gases therethrough, typically quartz has been used. Meanwhile, in the case where halogenous gas radicals are used, since these are particularly high corrosive, the gas tubes are readily corroded and require frequent replacement. Particularly, quartz is easily eroded by the halogenous radicals, specifically fluoric radicals, to thereby produce dust. The quartz, though it originally has a high UV transmittance, readily turns to opaque, resulting in decrease of the UV transmittance, especially due to corrosion with halogenous corrosive gas plasma.

SUMMARY OF THE INVENTION

It is, therefore, an object of the present invention to provide a gas tube for passing plasma generating gases therethrough, which has high UV transmittance and corrosion resistance against corrosive gas.

The present invention relates to a gas tube for passing a plasma generating gas therethrough and irradiating said gas with UV rays, during running in the tube, which tube is characterized by comprising a longitudinally extended throughhole for passing the plasma generating gas therethrough and a thin circumferential wall formed of a light-pervious alumina ceramic having a center-line mean roughness ($R_a$) of not more than 1.0 μm at a portion thereof to be exposed to gas plasma, and being provided with a UV radiating means for irradiating the gas running in the throughhole with UV rays from outside of the tube to generate gas plasma.

The "center-line mean roughness ($R_a$)" used throughout this specification, is defined in JIS B 0601-1982 as follows:

The center-line mean roughness, when the roughness curve has been expressed by y=f (x), shall be a value, being expressed in micrometer (μm), that is obtained from the following formula, extracting a part of measuring length l in the direction of its center-line from the roughness curve, and taking the center-line of this extracted part as X-axis and the direction of vertical magnification as Y-axis.

$$R_a = \frac{1}{l} \int_0^l |f(x)| dx$$

The inventors, in the course of an assiduous study on materials for the aforesaid gas tube, have found that a specific light-pervious alumina ceramic has an extremely high corrosion resistance against gas plasma as well as a high UV transmittance, and have eventually reached this invention.

Particularly, it was important to make a center-line mean roughness ($R_a$) not more than 1.0 μm at a portion to be exposed to gas plasma. The reason is conjectured that corrosive gas plasma runs along rugged rough surfaces of the tube, probably etching grain boundaries of alumina crystal grains whereby the ruggedness of the surface will be enlarged, until crystal grains are liberated. It has been found that this etching effect is extremely decreased by making a center-line mean roughness ($R_a$) not more than 1.0 μm at a portion to be exposed to the gas plasma, of the surface of the tube. Furthermore, devitrification caused by the gas corrosion of the surface was able to be prevented.

The present invention further relates to a gas tube for generating plasma, wherein a plasma generating gas is irradiated with UV rays, during running in the tube, which tube is characterized by comprising a longitudinally extended throughhole for passing the plasma generating gas therethrough and a thin circumferential wall, and being provided with a UV radiating means for irradiating the gas running in the tube with UV rays from outside of the tube, which tube is formed of a light-pervious alumina ceramic composed of alumina crystal grains having an average grain diameter of between 35 μm and 50 μm at a portion where the UV rays are directed and transmitted.

Namely, the present inventors have found that the average crystal grain diameter of the light-pervious alumina ceramic is important; for the UV transmittance is extremely increased when the average grain diameter is not less than 35 μm and the corrosion resistance against corrosive gases is increased when it is not more than 50 μm.

In a preferred embodiment of the invention, an annular disk is attached on the outer peripheral surface, perpendicularly to the longitudinal axis of the tube, and midway the longitudinal axis, which annular disk serves as a supporting brim for fixing the tube airtightly to a plasma treating chamber. This facilitates installation of the gas tube on the plasma treating chamber.

In this case, the annular disk can divide the tube into two portions: an upstream portion which is irradiated with UV rays (hereinafter referred to as "first portion"); and a downstream portion which is not irradiated with UV rays, both the entire inner and outer surfaces of which are exposed to gas plasma (hereinafter referred to as "second portion"). Further, it is preferred that both the inner and outer surfaces of the circumferential wall of the second portion and the inner surface of the circumferential wall of the first portion have a center-line wean roughness ($R_a$) of not more than 1.0 μm.

In this embodiment, it is further preferred to make the circumferential wall of the second portion thicker than that of the first portion. The first portion is required to increase the transmittance rate mainly of UV rays, preferably to 70% or more. The thinner the wall of the first portion, the higher the transmittance rate. On the other hand, the corrosion resistance against gas plasma is increased with increasing the circumferential wall thickness of the second portion, with the consequence that the life span of the gas tube can be extended before replacement.

From the above point of view, the first portion is preferred to have a wall thickness of not more than 0.8 mm, more preferably 0.5–0.8 mm. On the other hand, the second portion is preferred to have a wall thickness of not less than 1.0 mm, more preferably not less than 1.2 mm. Further, a quotient given by dividing the wall thickness of the second portion by that of the first portion is preferred to be not less than 2.0.

Further, in the first portion, the light-pervious alumina ceramic that constitutes the circumferential wall is preferred to be composed of alumina crystal grains having an average grain diameter of between 35 $\mu$m and 50 $\mu$m. On the other hand, in the second portion, the circumferential wall does not require a high UV transmittance rate. The second portion, since it is located contiguous to the chamber of the plasma treating apparatus, is required to have a corrosion resistance greater than that of the first portion. Therefore, the light-pervious alumina ceramic that constitutes the second portion is preferred to be composed of alumina crystal grains having an average grain diameter of not more than 35 $\mu$m, more preferably not more than 30 $\mu$m.

The light-pervious alumina ceramic is manufactured with a starting material preferably prepared from a 99.99% high purity alumina powder admixed with additives for controlling grain diameters during sintering. With this starting material, ceramic shaped bodies are fabricated by means of mechanical pressing, cold isostatic pressing, extrusion technique, or the like. The shaped bodies are then dewaxed and fired at 1,800°–1,900° C. in a hydrogen atmosphere. The fired bodies consist of a transparent ceramic composed of homogeneous hexagonal crystal grains. The thus obtained light-pervious alumina ceramics have been extensively used for light emitting tubes for high-intensity discharge (KID) lamps, such as high-pressure sodium discharge lamps and the like. The total light transmittance of the light-pervious alumina ceramics at a wavelength of 600 nm (a visible wavelength range) reaches 96% approximately.

As plasma generating gases, reactant gases such as $NF_3$, $CF_4$, $CHF_3$, $CCl_4$, $BCl_3$, $CCl_2F_2$ or the like can be used. These reactant gases may be admixed with oxygen, chlorine, helium, argon or the like for increasing the etching rate and selectivity.

BRIEF DESCRIPTION OF THE DRAWINGS

The above and other objects, features and advantages of the present invention will become more apparent from reading the following description of the preferred embodiments taken in connection with the accompanying drawings, wherein:

FIG. 2 is a graph showing a relationship between the thickness and UV transmittance with respect to each of test-pieces having different average grain diameters, cut out from a circumferential wall of a gas tube.

DESCRIPTION OF THE PREFERRED EMBODIMENTS

Figure 1:
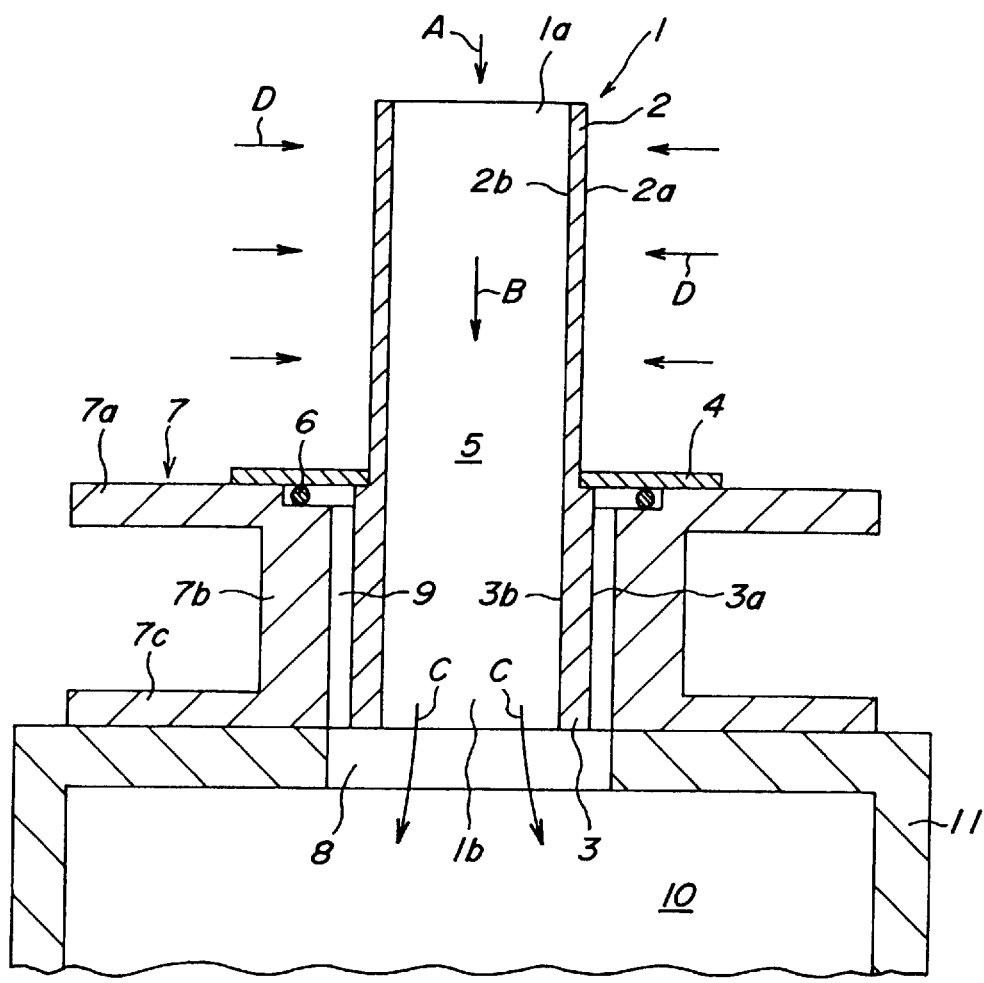
FIG. 1 is a vertical sectional view schematically illustrating the main portion of the plasma treating apparatus according to the preferred embodiment of the present invention.

In FIG. 1, a substrate to be treated is placed in a treating space 10 inside a chamber 11 of a plasma treating apparatus, wherein pattern-etching, cleaning, etc. are conducted by means of gas plasma. A double flanged bracket 7 is mounted on the rim of an aperture 8 of the chamber 11. The bracket 7 comprises a cylindrical body 7b and flanges 7a and 7c extending outward from two ends of the cylindrical body 7b, respectively. One flange 7c of the two is airtightly fixed to the chamber 11.

The gas tube according to this example comprises a circumferential wall 1 and an annular disk 4 which is airtightly fixed to the outer surface, perpendicularly to the longitudinal axis, of the circumferential wall 1. The circumferential wall 1 comprises a first portion 2, i.e. an upstream portion upward from the annular disk 4 and a second portion 3, i.e. a downstream portion downward from the annular disk 4, in FIG. 1. The outer peripheral surface 2a of the first portion 2 is not exposed to plasma generating gases. The annular disc 4 is fixed to the double flanged bracket 7 airtightly with a gasket, such as an O-ring 6, interposed therebetween. The second portion 3 is fixed, suspending in the inner space 9 defined by the bracket 7.

In operation, a plasma generating gas is fed from the inlet 1a to the gas tube as indicated with the arrow A into the passage 5 as indicated with the arrow B. Then, UV rays are radiated towards the gas running in the passage 5 from outside of the first portion 2 of the circumferential wall 1 as indicated with the arrows D. Then, the gas generating plasma runs through the second portion 3, and flows via the outlet 1b, into the chamber 11, as indicated with the arrows C. Therefore, the inner peripheral surface 2b of the first portion 2 and the inner and outer peripheral surfaces 3a and 3b of the second portion 3 are contacted with the plasma generating gas.

A further material experimental result will be explained hereinafter.

A gas tube as shown in FIG. 1 was manufactured and fixed on the chamber 11. More concretely, a high purity alumina starting powder was used. The purity of this powder was 99.99%. 48–50 parts by weight of this alumina starting powder were admixed with 50 parts by weight of pure water and 750 ppm as MgO of magnesium nitrate. The powder mixture was pulverized for 10–15 hours to provide slurry of 4.5–6.0 pH, comprising particles having an average particle diameter of 0.45 $\mu$m. This slurry was passed through a 44 $\mu$m mesh nylon sieve, then admixed with 3 parts by weight of an organic binder and stirred in a slurry tank. The slurry was granulated by means of a spray dryer and the obtained granulated powder was passed through a 149 $\mu$m mesh nylon sieve to provide powder for cold isostatic press (CIP) shaping.

In order to shape a gas tube, this powder was charged in a mold for CIP shaping. As the sheath of the mold, a urethane rubber mold was used and as the core of the mold, a core made of SKD-11 plated with hard chromium in a thickness of 10 $\mu$m was used. The mold was sealed, that was then placed in a vessel for CIP and pressurized at 1,850 kg/cm$^2$ to shape. The thus obtained tubular shaped body was removed from the mold.

On the other hand, in order to shape an annular disk 4, the aforementioned granulated powder was charged into another mold for CIP shaping. A urethane rubber mold was used as a mold. The mold was sealed, then placed in a vessel for CIP shaping and pressurized at 1,850 kg/cm$^2$ to shape. The thus obtained annular-disk-type shaped body was removed from the mold.

Subsequently, the outer peripheral surface of the tubular shaped body was ground into a uniform thickness between 1 mm and 1.5 mm. The tubular shaped body and the annular-disc-type shaped body were subjected to provisional firing in an oxidative atmosphere. The provisionally fired tubular shaped body was machined with a lathe, abraded with a #800 sandpaper, then buffed with cloth, and finally wiped up with cloth soaked in acetone.

The tubular shaped body and the annular-disc-type shaped body were bonded together with alumina paste. The thus conjoint body was heated at 850° C. in an oxidative atmosphere to dewax binder contained in the alumina paste, and then fired at a predetermined temperature of 1870° C. to 1900° C. in a hydrogen atmosphere. Then, both the opening ends of the tube were abraded and the whole gas tube was washed.

A test-piece was cut out from the thus obtained gas tube, and measured for UV transmittance. However, the measurement was conducted on various test-pieces different in the thickness and the average crystal grain diameter of the light-previous alumina ceramic constituting the test piece, as shown in Table 1. The center-line mean roughness ($R_a$) of each test-piece was set to be 1.0 μm. The results are shown in Table 1. Further, in FIG. 2, the graph shows a relationship between the thickness and UV transmittance with respect to each of test-pieces cut out from tubular shaped bodies having different average crystal grain diameters: 28 μm (plot A), 30 μm (plot B), 40 μm (plot C), and 35 μm (plot D).

In order to change the average crystal grain diameter of the light-pervious alumina ceramic which constitutes tube, the maximum temperature was set to 1900° C. sintering in a hydrogen atmosphere and the retention time of the maximun temperature was changed from 3 hours to 5 hours in the aforementioned manufacturing process.

TABLE 1

| Average gain diameter of light-pervious alumina (μm) | Thickness of test-piece (mm) | UV transmittance (%) |
|---|---|---|
| 28 | 0.4 | 72 |
| 28 | 0.5 | 69 |
| 28 | 0.7 | 60 |
| 28 | 0.9 | 57 |
| 30 | 0.2 | 80 |
| 30 | 0.25 | 78 |
| 30 | 0.5 | 69.5 |
| 30 | 1.0 | 62 |
| 35 | 0.4 | 77 |
| 35 | 0.6 | 72 |
| 35 | 1.0 | 66 |
| 40 | 0.4 | 81 |
| 40 | 0.5 | 79 |
| 40 | 0.6 | 76 |
| 40 | 0.8 | 73 |
| 40 | 1.0 | 70 |

As seen from these results, by making the average crystal grain diameter not less than 35 μm, the light-ceramic pervious alumina ceramic constituting the gas tube was extremely increased in the UV transmittance. Particularly, even when the wall thickness of the gas tube was 1.0–0.5 mm, the UV transmittance was sufficiently as high as no less than 70%.

Then, tests with respect to corrosion resistance against gas plasma in gas tubes were conducted. Test-pieces with a dimension of 10 mm×10 mm×0.5 mm made of the aforementioned light-pervious alumina ceramic, quartz and sapphire, respectively, were cut out and placed in a vacuum chamber. This vacuum chamber was equipped with a microwave oscillator. The test-pieces were heated at 500° C. with a heater and the pressure was reduced to 100 nm Torr. Then, $NF_3$ gas at a flow rate of 200 cc/minute and argon gas at a flow rate of 25 cc/minute at 0° C. under 1 atmospheric pressure were introduced into the chamber for 1.5 hours, wherein gas plasma was generated by means of a microwave of 13.56 MHz frequency generated with the microwave oscillator of 450W output. The test-pieces were weighed before and after the test, and weight differences were calculated. Then, etching rates were calculated from the weight differences. Additionally, the UV transmittances of the test-pieces before and after the test were determined.

Besides, with respect to the circumferential wall comprising a light-pervious alumina ceramic, the center-line mean roughness ($R_a$) and the average crystal grain diameter were changed as shown in Table 2. The results of the measurements are shown in Table 2.

TABLE 2

| Materials | Average crystal grain diameter (μm) | Ra (μm) | Surface area (cm²) | Density (g/cm³) | Etching rate (Å/Sec.) | UV transmittance before test (%) | UV transmittance after test (%) |
|---|---|---|---|---|---|---|---|
| Quartz | — | 0.2 | 2.0 | 2.21 | 3.50 | 98 | 95 |
| Sapphire | — | 0.1 | 2.0 | 3.99 | 0.25 | 86 | 86 |
| Light- | 30 | 1.1 | 2.0 | 3.99 | 0.05 | 65 | 64 |
| pervious | 30 | 0.5 | 2.0 | 3.99 | 0 | 69 | 69 |
| alumina | 40 | 1.1 | 2.0 | 3.99 | 0.05 | 75 | 74 |
| ceramic | 40 | 0.5 | 2.0 | 3.99 | 0 | 78 | 78 |

As mentioned above, according to the present invention, there can be the provision of gas tubes for passing plasma generating gases, which have a high UV transmittance and a corrosion resistance against corrosive gases.

What is claimed is:

1. A gas tube for passing a plasma generating gas therethrough and irradiating said gas with UV rays, during running in the tube, which tube comprises a longitudinally extended through-hole and a thin circumferential wall formed of a light-pervious alumina ceramic having a center-line mean roughness ($R_a$) of not more than 1.0 μm at a portion thereof to be exposed to gas plasma, and is provided with a means for radiating UV rays directed towards an upstream portion of the tube, from outside of the tube.

2. The gas tube according to claim 1, which is further provided with an annular disk attached on an outer peripheral surface of said circumferential wall, across and midway a longitudinal axis of the tube, which disk serves as a supporting brim for fixing the tube airtightly to a plasma treating chamber.

3. The gas tube according to claim 2, wherein said annular disk divides the tube into two portions: an upstream portion which is irradiated with UV rays; and a downstream portion which is not irradiated with UV rays and has inner and outer surfaces thereof entirely exposed to gas plasma, and both the inner and outer surfaces of the downstream portion and an inner surface of the upstream portion having a center-line mean roughness ($R_a$) of not more than 1.0 μm.

4. The gas tube according to claim 3, wherein said upstream portion towards which the radiating UV rays are directed is formed of a light-pervious alumina ceramic which is composed of alumina crystal grains having an average grain diameter of between 35 μm and 50 μm.

5. The gas tube according to claim 3, wherein the circumferential wall of the downstream portion is thicker than that of the upstream portion.

6. A gas tube for passing a plasma generating gas therethrough and irradiating said gas, during running in the tube, with UV rays, which tube comprises a longitudinally extended through-hole and a thin circumferential wall formed of a light-pervious alumina ceramic and is provided with a means for radiating UV rays directed towards an upstream portion of the tube, from outside of the tube, said light-pervious alumina being composed of alumina crystal grains having an average grain diameter of between 35 μm and 50 μm at a portion towards which the radiating UV rays are directed.

* * * * *

UNITED STATES PATENT AND TRADEMARK OFFICE
CERTIFICATE OF CORRECTION

PATENT NO. : 5,814,818
DATED : September 29, 1998
INVENTOR(S) : Toshio OHASHI et al.

It is certified that error appears in the above-indentified patent and that said Letters Patent is hereby corrected as shown below:

Column 1, line 29, change "high" to --highly--.

line 34, cancel "to"; and insert --a-- after "in";
            lines 47 and 48, change "is characterized by comprising" to --has--;
            line 54, change "being" to --is--; and
            line 63, change "micrometer" to --micrometers--.

Column 2, line 14, change "The reason is conjectured" to --It is believed--;
            line 28, change "is characterized by comprising" to --has--;
            line 30, change "being" to --is--;
            line 45, insert --of-- before "the"; and
            line 66, change "with" to --by--.

Column 3, line 18, change "plasma treating" to --plasma-treating--; and
            line 54, change "plasma treating" to --plasma-treating--.

Column 4, line 52, change "that was" to --and--.

Column 5, line 15, cancel "the" (both occurrences); and
            line 22, insert --the-- after "of".

UNITED STATES PATENT AND TRADEMARK OFFICE
CERTIFICATE OF CORRECTION

PATENT NO. : 5,814,818
DATED : September 29, 1998
INVENTOR(S) : Toshio Ohashi, et. al.

It is certified that error appears in the above-identified patent and that said Letters Patent is hereby corrected as shown below:

Column 6, line 1, cancel "the"; and line 44, change "the provision of" to --produced--.

Signed and Sealed this

Sixth Day of April, 1999

Attest:

Attesting Officer

Q. TODD DICKINSON

Acting Commissioner of Patents and Trademarks